(12) United States Patent
Oakley et al.

(10) Patent No.: US 10,441,721 B2
(45) Date of Patent: Oct. 15, 2019

(54) DRUG DELIVERY DEVICE

(71) Applicant: Sanofi, Paris (FR)

(72) Inventors: Tom Oakley, Cambridge (GB); Karl Hewson, Cambridge (GB); Stuart Milne, Buckden St. Neots (GB); Mark Pawulski, Buckingham (GB)

(73) Assignee: Sanofi, Paris (FR)

( * ) Notice: Subject to any disclaimer, the term of this patent is extended or adjusted under 35 U.S.C. 154(b) by 647 days.

(21) Appl. No.: 14/905,080

(22) PCT Filed: Jul. 17, 2014

(86) PCT No.: PCT/EP2014/065344
§ 371 (c)(1),
(2) Date: Jan. 14, 2016

(87) PCT Pub. No.: WO2015/007825
PCT Pub. Date: Jan. 22, 2015

(65) Prior Publication Data
US 2016/0166775 A1  Jun. 16, 2016

(30) Foreign Application Priority Data

Jul. 17, 2013 (EP) .................................... 13176888

(51) Int. Cl.
*A61M 5/31* (2006.01)
*A61M 5/315* (2006.01)

(52) U.S. Cl.
CPC .... *A61M 5/31528* (2013.01); *A61M 5/31548* (2013.01); *A61M 2005/3125* (2013.01); *A61M 2205/33* (2013.01); *A61M 2205/581* (2013.01)

(58) Field of Classification Search
CPC .............. A61M 5/3125; A61M 5/3128; A61M 5/31548; A61M 5/3155;
(Continued)

(56) References Cited

U.S. PATENT DOCUMENTS 6,547,763 B2 * 4/2003 Steenfeldt-Jensen ....................... A61M 5/31553 604/181
8,357,120 B2 * 1/2013 Moller .............. A61M 5/14566 604/135

(Continued)

FOREIGN PATENT DOCUMENTS

| EP | 1 642 607 | 4/2006 |
|---|---|---|
| JP | 2013-528090 | 7/2013 |

(Continued)

OTHER PUBLICATIONS

International Preliminary Report on Patentability in International Application No. PCT/EP2014/065344, dated Jan. 19, 2016, 7 pages.

(Continued)

*Primary Examiner* — Jason E Flick
*Assistant Examiner* — Courtney B Fredrickson
(74) *Attorney, Agent, or Firm* — Fish & Richardson P.C.

(57) ABSTRACT

The invention relates to a drug delivery device for selecting and dispensing a number of user variable doses of a medicament. The device comprises a dosing element (40, 30), which rotates in a first direction during dose selecting and rotates in a second, opposite direction during dose dispensing, and a display (60) for indicating the selected dose. The display (60) comprises at least one belt (61, 62) having symbols for indicating the selected dose and being coupled to the dosing element (40, 130) such that a rotation of the dosing element (40, 130) spools the belt (61, 62).

17 Claims, 6 Drawing Sheets

(58) Field of Classification Search
CPC ...... A61M 2005/3126; A61M 5/31526; A61M 5/31533; A61M 5/31545; A61M 5/31558; A61M 2005/3125; A61M 5/31551
See application file for complete search history.

(56) References Cited

U.S. PATENT DOCUMENTS

| | | | |
|---|---|---|---|
| 2005/0177114 A1* | 8/2005 | Michel | A61M 5/31553 604/207 |
| 2015/0065963 A1* | 3/2015 | Kjeldsen | A61M 5/31541 604/207 |
| 2016/0030678 A1* | 2/2016 | Bayer | A61M 5/20 604/211 |

FOREIGN PATENT DOCUMENTS

| WO | WO 2001/087386 | 11/2001 |
|---|---|---|
| WO | WO 2004/078241 | 9/2004 |
| WO | WO 2011/154488 | 12/2011 |
| WO | WO 2012/130991 | 10/2012 |
| WO | WO 2012/164097 | 12/2012 |

OTHER PUBLICATIONS

International Search Report and Written Opinion in International Application No. PCT/EP2014/065344, dated Oct. 1, 2014, 10 pages.

* cited by examiner

Figure 1
Figure 2
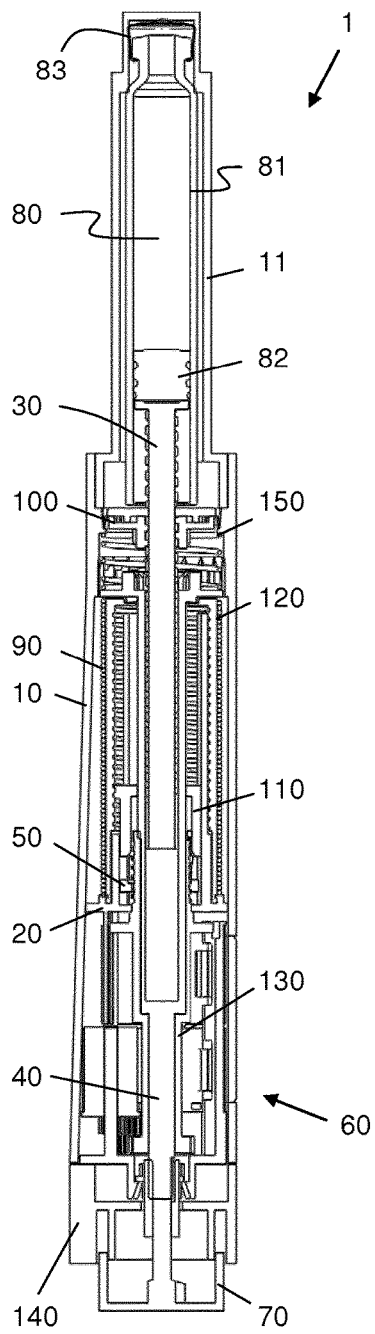
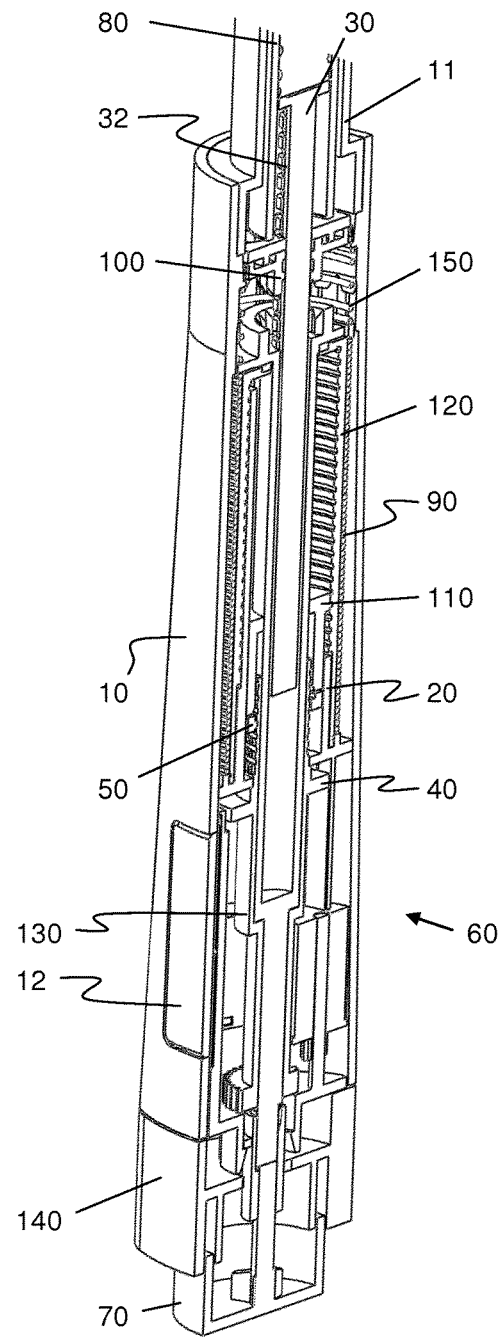

DRUG DELIVERY DEVICE

CROSS-REFERENCE TO RELATED APPLICATIONS

This application is a U.S. national stage application under 35 USC § 371 of International Application No. PCT/EP2014/065344, filed on Jul. 17, 2014, which claims priority to European Patent Application No. 13176888.9, filed on Jul. 17, 2013, the entire contents of which are incorporated herein by reference.

The present invention is generally directed to drug delivery devices. In more detail, the invention refers to a display which is typically used for indicating the selected dose of a drug delivery device.

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present invention is not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present invention is applicable for both types of devices, i.e. for disposable devices as well as for reusable devices.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting. The present invention is applicable for all of these types of devices, i.e. for devices with or without a drive spring.

These types of pen delivery devices (so named because they often resemble an enlarged fountain pen) are generally comprised of three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

The dosing section of drug delivery devices for selecting and dispensing a number of user variable doses of a medicament often comprises a display for indicating the selected dose to a user. This is especially important where a user may select a different dose each time depending on the state of health. There are mechanical displays, e.g. a drum with printed numbers on its outer surface, wherein the number corresponding to the actually selected dose is visible through a window or opening in the device. Although such mechanical displays are simple and reliable, they usually require a relatively large construction space which makes the devices bulky. In addition, the size of the numbers is in some cases too small for visually impaired users. Further, electronic displays are known, e.g. LCD displays, which have the benefit of a relatively large number size without requiring too much construction space. However, a downside of electronic displays is that they require an energy source and that such electronic components may be too expensive, especially in a disposable drug delivery device.

A disposable drug delivery device for selecting and dispensing a number of user variable doses of a medicament according to the present invention typically comprises a dosing element, which rotates in a first direction during dose selecting and rotates in a second, opposite direction during dose dispensing, and a display for indicating the selected dose.

Such a disposable drug delivery device is known from WO 2004/078241 A1, wherein the display comprises a number sleeve with numbers printed on its outer surface. The device further comprises a housing, a cartridge holder for retaining a cartridge containing a medicament, a piston rod displaceable relative to the cartridge holder, a driver coupled to the piston rod, a dose setting knob coupled to the driver and fixed to the number sleeve, and an injection button. The number sleeve is in threaded engagement with the housing, such that the number sleeve rotates along a helical path in a first direction during dose selecting and rotates back into the housing in a second, opposite direction during dose dispensing.

WO 01/87386 A1 discloses a dose display comprising at least one flexible disc which is driven by a dose setting grip during dose selecting and dose dispensing such that the disc performs a mere rotation.

EP 1 642 607 A1 discloses a first ring of digits on a dose setting dial and a further ring of digits on a counter ring which are used in a dose display of a drug delivery device.

In WO 2012/164097 A1 a band-like dose dial scale is coupled to a user operable control member. Further, in US 2005/0177114 A1 a rotational button is provided for setting a dose which is coupled to a scale band. However, WO 2012/164097 A1 and US 2005/0177114 A1 do not disclose a dose setting element which rotates in a second opposite direction during dose dispensing.

It is an object of the present invention to provide an improved drug delivery device which has a display for conveniently indicating the selected dose even for visually impaired users. Preferably, the display allows easy handling of the device and is reasonable regarding costs even for disposable devices. It is a further object to provide a simple and yet reliable display for e.g. use in a drug delivery device.

According to a first embodiment of the present invention, this object is solved by a drug delivery device comprising a dosing element, which rotates in a first direction during dose selecting and rotates in a second, opposite direction during dose dispensing, and a display for indicating the selected dose, wherein the display comprises at least one belt having symbols for indicating the selected dose and being coupled to the dosing element such that a rotation of the dosing element moves or shifts the belt.

The term belt defines any thin non-rigid member having an extension in one direction (length) which is much bigger than in the two other directions (thickness and width), i.e. for example a film or a tape-like member. A belt according to the present invention may be provided e.g. with the numbers indicative of dose values.

The rotational movement of the dosing element is used to drive the belt. Typically, the movement of the belt is a spooling motion. A spooling motion is according to the present invention a motion coiling the belt from a first spool to a second spool. Thus, the spooling motion includes a translational displacement of the portion of the belt located between the spools. The dosing element may alternatively move non-rotationally and drive the belt by, for example, a screw thread, rack and pinion gear, or cam or suchlike.

Rotation of the dosing element in a first direction during dose selecting does not exclude that the dose can be reduced as well as increased during dose setting, which might involve rotation in the opposite direction.

The dosing element may be any suitable component part of the drug delivery device which performs a rotational movement both during dose setting, i.e. increasing or decreasing the selected dose, and during dose dispensing. This results in the belt being spooled not only during dose setting but also during dose dispensing, such that after dispensing a set dose the display indicates that the dose has been fully administered and/or is ready for the next dose selection. Although it is preferred if the dosing element performs a pure rotational movement during dose setting and dose dispensing, i.e. not a combined axial and rotational movement, it is also possible to drive the belt with a dosing element which travels on a helical path during dose setting and/or dose dispensing. The term dosing element is not intended to limit said element to a component which has the sole or main function to select a dose. Moreover, any component part rotating during dose setting and dose dispensing may be the dosing element, even if its main function is e.g. to drive the piston rod, to strain a spring, to transfer a movement from one component part to another, or the like.

The use of a belt in the display has the benefit that relatively large sized numbers can be accommodated in a small construction space. This is possible as the belt may be wound on or around spools or deflection pulleys. Further, the belt may be relatively thin compared with a threaded number sleeve.

A preferred embodiment of the invention comprises a drug delivery device wherein the (or at least one) belt is directly coupled to the dosing element. An example of this embodiment is a cam belt which is driven by a gear of the dosing element. As an alternative, the belt may be driven by the dosing element similar to a film-tape, i.e. with a series of apertures in the belt and corresponding protrusions on the dosing element. Preferably, the dosing element comprises a sprocket with the belt engaging the sprocket.

According to an additional or alternative embodiment, the (or at least one) belt is indirectly coupled to the dosing element. This allows moving or spooling the belt with a different velocity compared with the rotational speed of the dosing element. In a simple and yet reliable preferred example the dosing element comprises at least one drive gear which is coupled to a sprocket, wherein the belt engages the sprocket. In other words, a gearbox assembly is interposed in the drive train between the dosing element and the belt.

In some cases it might be useful for the display of a drug delivery device not to indicate a small rotation of the dosing element. This may occur if the belt is not provided with numbers, symbols or the like for every dose increment the dosing element is rotated. In other words, the display may indicate only every ten dose units instead of every single dose unit. In such cases it might be desirable that the display is not in an intermediate position, e.g. between two numbers. Thus, the belt may be coupled to the dosing element such that a continuous rotation of the dosing element is translated into an intermittent motion of the belt. An example for a belt which is indirectly coupled to the dosing element is a Geneva drive. An example for a belt which is directly coupled to the dosing element is a transmission similar to a film-tape, where the distance between the protrusions on the dosing element exceeds the distance between the apertures in the belt.

According to a preferred embodiment, the display comprises a belt which is indirectly coupled to the dosing element and a further belt which is directly coupled to the dosing element. Typically, one of these belts is used to display the single digits whereas the other belt is used to display the tens of a two-digit or a more-digit number. For example in this case, the belt may be coupled to the dosing element such that a continuous rotation of the dosing element is translated into a continuous motion of the belt, and the further belt may be coupled to the dosing element such that a continuous rotation of the dosing element is translated into an intermittent motion of the further belt. Thus, the belt may be used to display the units and the further belt may be used to display the tens. If the maximum selectable dose of a device is e.g. 120 IU of insulin formulation, the belt comprises the numbers zero to nine and the further belt comprises the numbers zero to twelve.

In prior art drug delivery devices which use a drum or sleeve to display the numbers, the curvature of the drum or sleeve might cause drawbacks regarding the visibility of the numbers. With the belt type display of the present invention, this effect may be alleviated or fully removed by guiding the visible part of the belt in a plane. Preferably, a striker plate is provided which forms a flat or arced plane for guiding the at least one belt.

The belt may form a closed loop. As an alternative, the belt has two ends each being attached to a spool or the like.

The display according to the present invention may be used in different types of drug delivery devices. Preferably, the device further comprises a housing, a cartridge holder for retaining a cartridge containing the medicament, a piston rod displaceable relative to the cartridge holder, a driver coupled to the piston rod and at least one clutch. However, none of these component parts is essential for a drug delivery device using such a display. Rather, the display may be used in a device without a cartridge holder or a device not requiring a piston rod, e.g. a device where a spring acts on a cartridge bung, or a device without a driver, e.g. if the dosing element acts on the piston rod or directly on the cartridge bung. The clutch preferably decouples the driver and the dosing element during dose selecting and couples the driver and the dosing element during dose dispensing.

To reduce the dispensing force a user has to apply, the drug delivery device may further comprise an elastic element such as a spring for driving the dosing element during dose dispensing. In a disposable device, the spring may be a preloaded spring, i.e. a factory preloaded spring charged for the lifespan of the device. As an alternative, e.g. for a reusable device, the spring may be loaded during dose setting and releases the stored energy during dose dispensing. Either a disposable or a reusable device may use a combination of factory-set preload and user-generated load of the spring. Typical spring types suitable for a drug delivery device include a torsion spring, a tension spring or the like.

The drug delivery device may comprise a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4 (1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned poly-saccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immuno-globulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intra-chain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while p and c have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The object of the present invention is further solved by a display, e.g. for indicating the selected dose of a drug delivery device. The display preferably comprises a belt and at least one further belt, wherein the belts each having symbols for indicating the selected dose. The belts may be coupled to each other via a transmission or gearing such that a continuous motion of one of the belts is translated into an intermittent motion of the at least one further belt. This allows providing a display for a large number of units which has a small construction space. For example, one belt may be used to display the ones, i.e. numbers from zero to nine, and a further belt may be used to display a second digit of a two-digit number, i.e. the tens.

Exemplary embodiments of the invention will now be described with reference to the accompanying drawings, in which:

FIG. 1 shows a sectional view of a drug delivery device in accordance with the present invention;

FIG. 2 shows a cut-away view of a drug delivery device of FIG. 1;

Figure 5A:
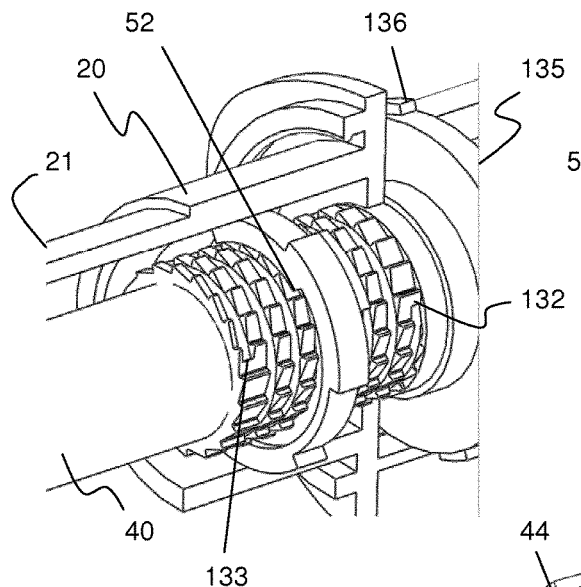
Figure 6:
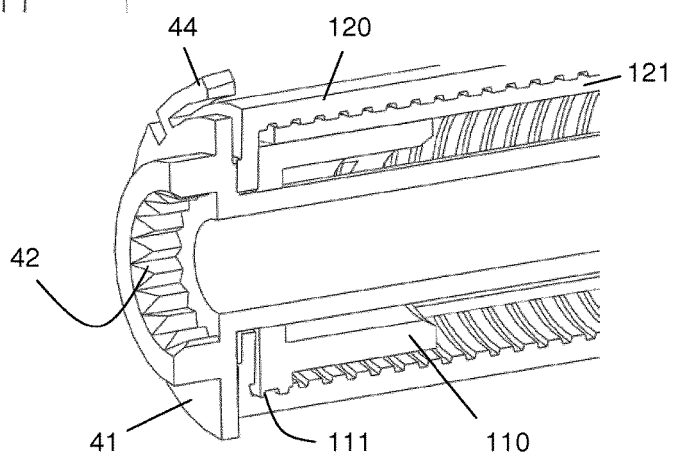
Figure 7A:
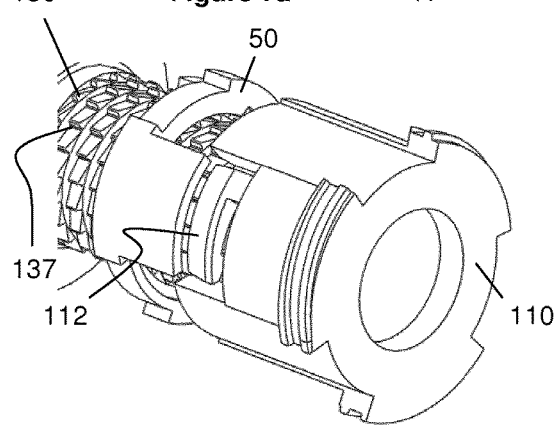
Figure 7B:
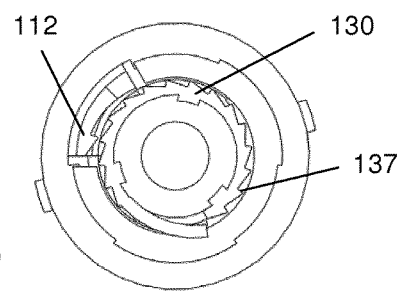
Figure 8:
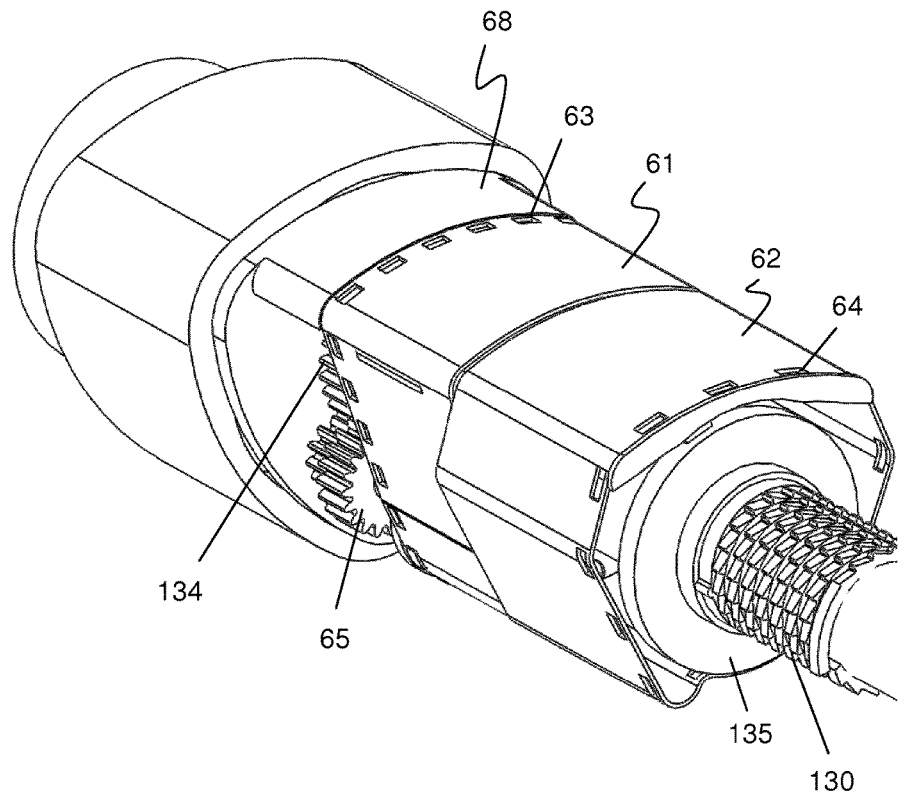
Figure 9:
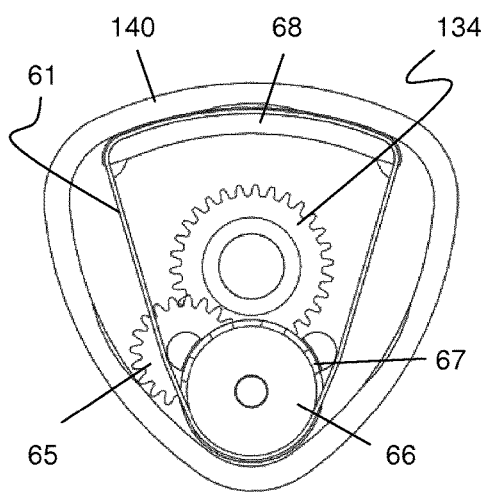
Figure 10:
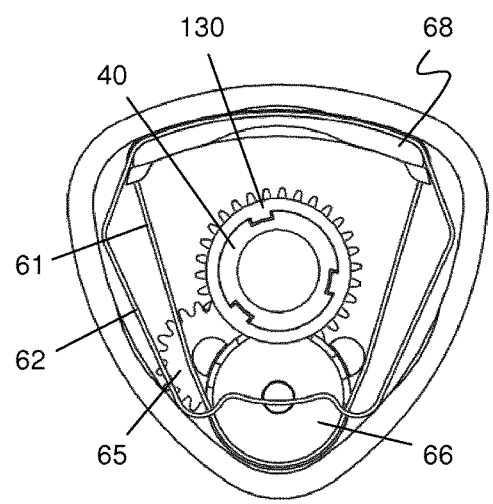
Figure 11:
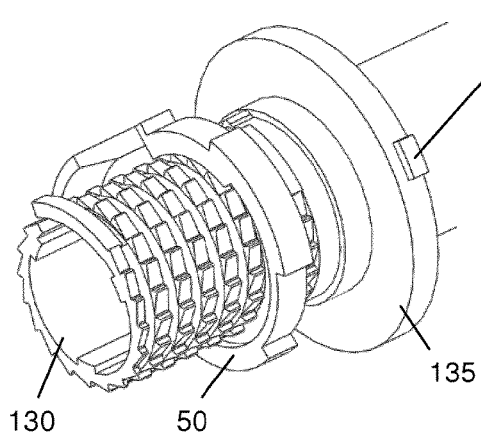
Figure 12:
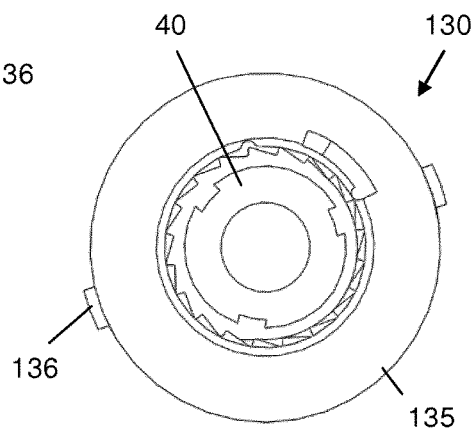
Figure 13A:
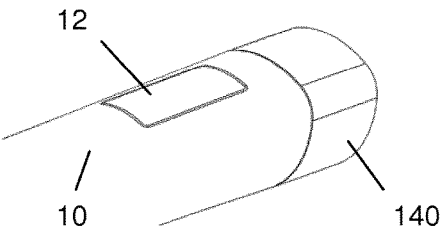
Figure 14:
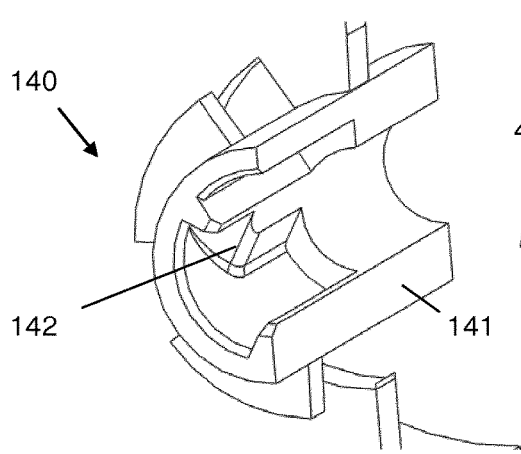
Figure 15:
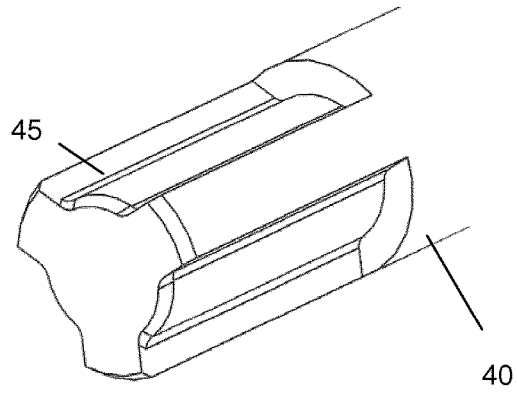
Figure 16A:
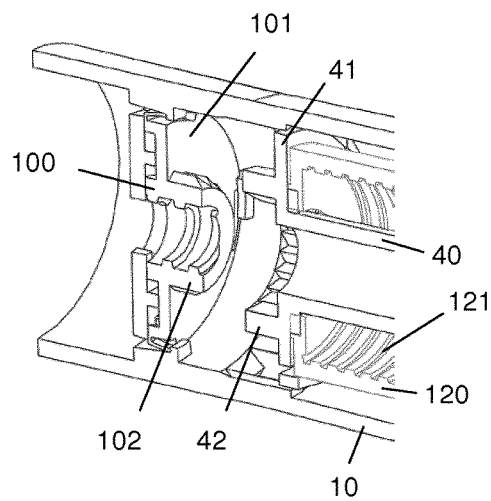
Figure 17A:
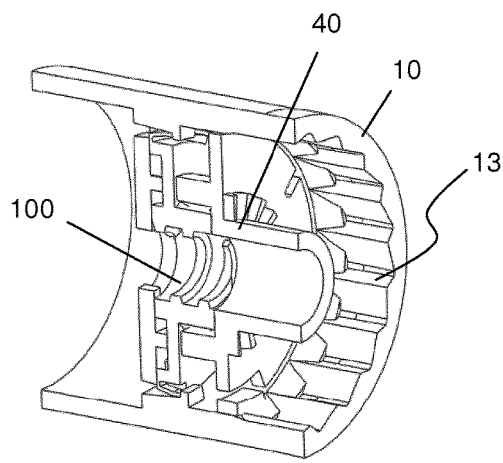
Figure 16B:
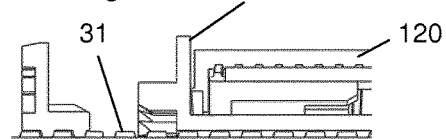
Figure 17B:
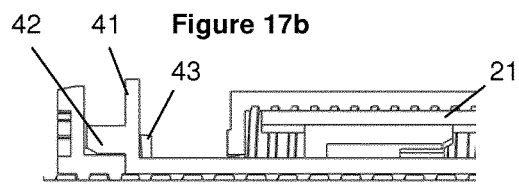
Figure 16C:
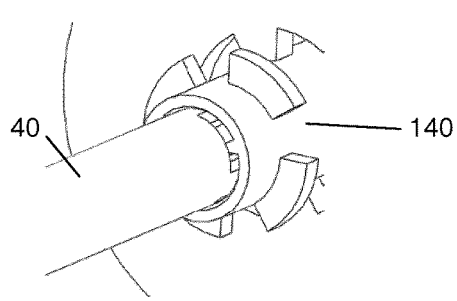
Figure 17C:
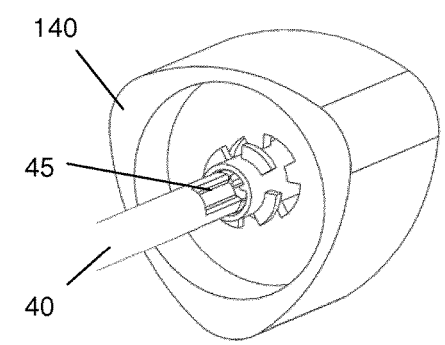

FIGS. 5a, b show cut-away views of a further detail of the drug delivery device of FIG. 1;

FIG. 6 shows a cut-away view of a further detail of the drug delivery device of FIG. 1;

FIG. 7a shows a cut-away view of a detail of the drug delivery device of FIG. 1;

FIG. 7b shows a sectional view of the detail of FIG. 7a;

FIG. 8 shows a cut-away view of the display of the drug delivery device of FIG. 1;

FIG. 9 shows a sectional view of the display of FIG. 8;

FIG. 10 shows a sectional view of the display of FIG. 8;

FIG. 11 shows a cut-away view of a further detail of the drug delivery device of FIG. 1;

FIG. 12 shows a sectional view of the detail of FIG. 11;

FIGS. 13a, b show perspective views of the proximal end of the drug delivery device of FIG. 1 in different positions;

FIG. 14 shows a cut-away view of a detail of the drug delivery device of FIG. 1;

FIG. 15 shows a perspective view of a detail of the drug delivery device of FIG. 1;

FIGS. 16a-c show cut-away views of details of the drug delivery device of FIG. 1 during dose setting; and FIGS. 17a-c show cut-away views of details of the drug delivery device of FIG. 1 during dose dispensing.

Figure 3:
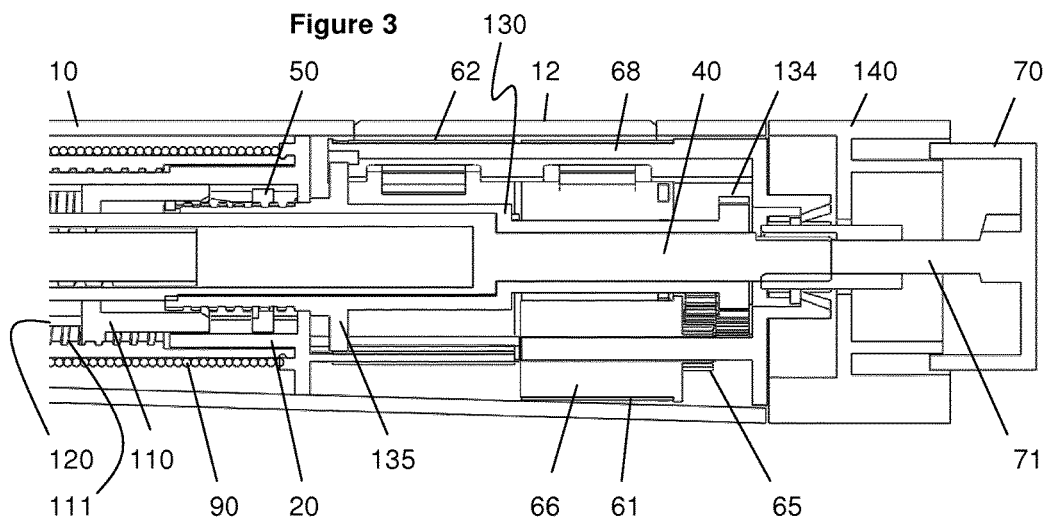
FIG. 3 shows an enlarged detail of FIG. 1.

FIG. 1 shows a drug delivery device 1 in the form of an injection pen. The device has a distal end (upper end in FIG. 1) and a proximal end (lower end in FIG. 1). The component parts of the drug delivery device 1 are shown in FIGS. 2 and 3 in more detail. The drug delivery device 1 comprises an outer housing 10, an inner body or chassis 20, a piston rod 30, a driver 40, a nut 50, a display 60, a button 70, a cartridge 80, a torsion spring 90, a drive nut 100, a last dose nut 110, a last dose sleeve 120, a transfer sleeve 130, a dose selector 140 and a return spring 150. A needle arrangement (not shown) with a needle hub and a needle cover may be provided as additional components, which can be exchanged as explained above.

The outer housing 10 is a generally tubular element having a distal part, which forms a cartridge holder 11 for receiving cartridge 80, and a proximal part for receiving the dosing mechanism. In a preferred embodiment, the outer housing 10 has a circular cross-section in the region of the cartridge holder 11 and in the intermediate region where the cartridge holder merges with the outer housing part covering the dosing mechanism, whereas the proximal region of the housing 10 has a (possibly rounded) triangular cross-section. Thus, it is comfortable to hold and handle the device 1. A window 12 is provided in the outer housing 10 allowing view of a detail of the display 60. The window 12 may, for example, be a substantially transparent component, or a substantially transparent region of a label applied to the housing 10, or omitted (leaving an empty viewport). The cartridge holder 11 may be a single-component part with the outer housing 10 or a separate component part attached to the outer housing 10 during assembly. As explained below in more detail, a portion of the outer housing 10 is provided with radially inwardly orientated teeth 13 forming a clutch with driver 40.

The chassis 20 is a generally tubular element which is axially and rotationally fixed within the outer housing 10. A flange may be provided attach a fee end of spring 90. Further, a splined finger 21 is provided which extends in the distal direction.

The piston rod 30 is an elongate element having an external thread 31 which engages the drive nut 100. Further, the piston rod comprises a spline 32 or the like alignment means for rotationally coupling the piston rod 30 in the outer housing 10 but allowing axial displacement of the piston rod 30 relative to the outer housing 10.

The driver 40 has a generally tubular distal portion which at least partly surrounds the piston rod 30. A proximal portion of the driver may have a smaller diameter. This proximal portion is a solid bar in the embodiment depicted in the figures but may as well have the cross-section of a circle (tubular), a cross (cruciform), a Y or suchlike. A flange 41 is provided at the distal end of the driver 40. As will be explained below in more detail, the flange comprises distally orientated teeth 42 forming a clutch which couples or decouples the driver to the drive nut 100. Further teeth 43 are provided on the proximal face of the flange 41 which are part of a clutch which couples or decouples the driver to the last dose sleeve 120. The driver 40 is splined to the transfer sleeve 130 to prevent relative rotation.

Figure 4:
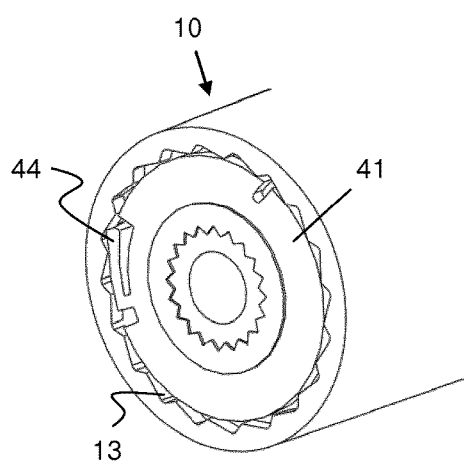
FIG. 4 shows a sectional view of a detail of the drug delivery device of FIG. 1.

In addition, a clutch is provided between the radially outer surface of flange 41 and outer housing 10. As shown in FIG. 4, this clutch may be formed as a ratchet with a ratchet finger 44 on the driver 40 and teeth 13 on an inner surface of the outer housing 10. The clutch allows stepwise rotation in a first direction during dose setting (dose increasing) but is designed to withstand the torque of torsion spring 90. The clutch is designed such that a user can overcome the clutch, i.e. reduce a set dose such that finger 44 overrides teeth 13 in a rotation opposite the first direction.

The nut 50 is provided between the transfer sleeve 130 and the chassis 20. External ribs of the nut 50 engage inner splines of the chassis 20. An internal thread of the nut 50 engages an external thread of the transfer sleeve 130. As an alternative, splines and ribs could be provided on the interface between the nut 50 and the transfer sleeve 130 and threads could be provided on the interface between the nut 50 and the chassis 20. As a further alternative, the nut 50 may be designed as e.g. a half nut.

Figure 5B:
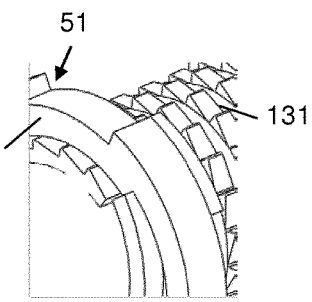

Further, in the embodiment of FIGS. 5a, 5b and 11, rotational hard stops 51, 52 are provided on nut 50 for interaction with corresponding stops on the transfer sleeve 130.

The display 60 comprises in the embodiment shown in FIGS. 8 to 10 a first belt 61 and a second belt 62 each having a series of numbers or the like symbols thereon and each having a series of apertures 63 and 64, respectively, which are arranged in uniform distribution with equal distance between the apertures. However, the size and/or the distances between apertures 63 and between apertures 64 may be different. The first belt 61 is driven via a drive gear 134 provided on the transfer sleeve 130, a transfer gear set 65, having two rotationally coupled gear wheels, and a transfer gear and sprocket set 66. A first gear wheel of the transfer gear set 65 meshes with the drive gear 134 and the second gear wheel of the transfer gear set 65 meshes with a transfer gear wheel of the transfer gear and sprocket set 66, which further comprises a sprocket rotationally coupled to the transfer gear wheel and engaging with protrusions 67 the apertures 63 of the first belt. Thus, rotation of the transfer sleeve 130 spools the first belt 61. The second belt 62 is driven by a sprocket 135 of the transfer sleeve 130 which has in the embodiment shown in the Figures two protrusions 136 engaging the apertures 64 in the second belt 62. Thus, the second belt 62 is directly coupled to the transfer sleeve 130. As the distance between protrusions 136 is much bigger than the distance between apertures 64, a continuous rotation of the transfer sleeve 130 is translated into an intermittent motion of the second belt 62.

Both belts 61, 62 are guided on a striker plate 68 which is fixed within the outer housing 10. The striker plate 68 has a flat or arched surface such that the part of the belts guided on the striker plate 68 has a curvature which is lower than the curvature of the cylindrical portion of the outer housing 10. Due to the striker plate 68, the outer housing 10 has its (rounded) triangular shape as indicated in FIGS. 9 and 10. In the embodiment depicted in the Figures, the first belt 61 is guided by the striker plate 68 and the sprocket of the transfer gear and sprocket set 66 on a generally triangular closed loop. The second belt may further be guided by suitable means to form a folded closed loop as indicated in FIGS. 8 and 10. The striker plate 68 may include one or more flexible features that may act to tension one or more belts. Similarly, other components may act to tension the belt, possibly in conjunction with the striker plate 68.

The button 70 forms the proximal end of the device and is held within dose selector 140 to allow relative rotation to the dose selector 140 and limited axial movement. A centrally located stem 71 abuts with its distal end face the proximal end face of the proximal part of driver 40. Thus, axial movement of button 70 is directly transferred to driver 40, although some embodiments allow some axial relative motion, which may be to improve usability or robustness to manufacturing tolerances.

The cartridge 80 includes a pre-filled, necked-down cartridge reservoir 81, which may be typically made of glass. A rubber type bung 82 or stopper is located at the proximal end of the cartridge reservoir 81, and a pierceable rubber seal (not shown) is located at the other, distal, end. A crimped annular metal band 83 is used to hold the rubber seal in place. The cartridge 80 is provided within the cartridge holder 11 with piston rod 30 abutting bung 82.

The drug delivery device 1 is intended to accept a 1.5 mL cartridge or a 3.0 mL cartridge, but the design could be adapted to accept other medicament container sizes or formats. The embodiment of the device depicted in the Figures is designed to be disposable in that the cartridge 80 cannot be replaced by the user or healthcare professional. A reusable variant of the device would involve making the cartridge holder removable and allowing the resetting of the piston rod 30.

The torsion spring 90 has two free ends, wherein the distal end is attached to the flange 41 of the driver 40 and the proximal end is attached to a flange of the stationary chassis 20. Thus, rotation of the driver 40 relative to the chassis 20 strains the torsion spring 90 and the stored energy may be released by allowing the driver 40 to rotate relative to the chassis 20. The torsion spring 90 may be assembled in a pre-loaded state to provide sufficient torque even for dispensing small doses. In an alternative embodiment the spring may be preloaded such that the stored energy is sufficient to dispense the whole contents of a full cartridge.

The drive nut 100 is a sleeve-like or disk-shaped component which has an inner thread engaging the thread 31 of the piston rod 30. The drive nut 100 is held within the outer housing 10 such that the drive nut 100 is allowed to freely rotate. In the embodiment shown in the Figures, the drive nut 100 comprises a flange 101 which forms a contact surface for the return spring 150 which is interposed between the driver 40 and the drive nut 100. Further, teeth 102 are provided for engagement with teeth 42 of driver 40.

The last dose nut 110 is provided interposed between the driver 40 and the chassis finger 21. A splined engagement between the chassis finger 21 and the drive nut 110 allows axial movement of the last dose nut 110 but prevents relative rotation with respect to the chassis 20. The last dose nut is provided with an outer thread 111.

The last dose sleeve 120 cooperates with the last dose nut 110 and nut 50 to form a last dose mechanism preventing setting of a dose which increases the amount of liquid left in the cartridge 80. The last dose sleeve 120 is a hollow component having an internal thread 121 which engages outer thread 111 of the last dose nut 110. A distal end face of the last dose sleeve 120 is provided with teeth 122 interacting with the teeth 43 provided on the proximal face of the flange 41 for rotationally coupling the last dose sleeve 120 to the driver 40.

The transfer sleeve 130 is a tubular element which is splined to the driver 40 such that it is rotationally constrained to the driver 40 but allows relative axial movement with respect to the driver. As mentioned above, the transfer sleeve 130 has a distal portion provided with thread 131 and rotational stops 132, 133. Further, the transfer sleeve 130 is provided with gear 134 for driving the first belt 61 and a sprocket 135 for driving the second belt 62. A stepped portion of the transfer sleeve 130 corresponds to the change in diameter of the driver 40 such that axial movement of the driver 40 relative to the transfer sleeve 130 is limited in the proximal direction.

The dose selector 140 has a triangular outer shape which may correspond to the outer shape of the proximal part of the outer housing 10. The dose selector 140 comprises an inner sleeve 141 guiding the stem 71 of the button 70 and receiving the proximal end of driver 40. As depicted in FIGS. 14 and 15 the proximal end of driver 40 has splines 45 engaging an inner guiding contour of the dose selector.

The return spring 150 is a compression spring which is located between flange 101 of drive nut 100 and flange 41 of driver 40. Thus, return spring 150 urges the driver 40 in the proximal direction. If button 70 is pushed by a user, driver 40 is moved in the distal direction against the bias of return spring 150.

In the following, the function of the disposable drug delivery device 1 and its components will be explained in more detail.

To use the device, a user has to select a dose. In the start (at rest) condition as shown in FIGS. 1 to 3 and 16a to 16c the torsion spring 90 has enough preload such that if the user selects the minimum dose the device will be able to deliver that minimum dose. At rest the dose indicator belts 61, 62 display 0 or the equivalent marking to show that no dose has been selected.

One or more priming and/or safety shots may be required prior to an injection. Priming is the act of preparing the device for first use. In existing pen injectors this means setting and delivering one or more small doses into air so that the 'play' (any clearances) and tolerances in the device are removed and that components are placed into suitable compression or tension. Safety shots are where the user sets and delivers one or more small doses into air before each injection to ensure that the needle is not blocked.

The user sets a dose by rotating the dose selector 140. Rotating the dose selector 140 rotates the driver 40 and adds preload to the torsion spring 90. The transfer sleeve 130 is splined to the driver 40 and indexes the dose number mechanism of display 60 when the user dials the dose selector 140.

FIG. 4 shows one or more ratchet features 44 on the driver 40 that engage with splines 13 on the internal surface of the outer housing 10 to prevent the dose selector 140 rotating back to its initial position due to the torsion spring torque. The ratchet feature(s) 13, 44 become disengaged when the user fully depresses the injection button 70.

Limits for a minimum dose (for example 0 IU of insulin formulation) and a maximum dose (for example 120 IU of insulin formulation) are provided by hard stop features on the nut 50 which interfere with features 132, 133 on the transfer sleeve 130 and therefore prevent further relative rotation. FIGS. 5a and 5b show the nut 50 in an intermediate position, i.e. with about 60 IU of insulin formulation dialled.

A last dose protection mechanism prevents the user from setting a dose greater than the available volume in the cartridge 80. During dose setting, the driver 40 is engaged with the last dose sleeve 120 via teeth 43 and 122. The last dose nut 110 is threaded to the last dose sleeve 120 and splined to the finger 21 of chassis 20 such that dialling the dose selector 140 up or down moves the last dose nut 110 left or right along the device (as seen in FIG. 6).

When the volume of drug formulation remaining in the cartridge 80 falls below the maximum normal settable dose (for example 120 IU of insulin formulation) the last dose nut 110 has moved in to a position where it can interfere with the nut 50. When the user attempts to dial a dose greater than that remaining, the nut 50 bends a flexible feature 112 on the last dose nut 110 such that it engages with step-like spline features 137 on the transfer sleeve 130 to form a rotary hard stop. FIGS. 7a and 7b show the device shortly before engagement of this last dose mechanism.

The indicated dose number is increased or reduced as the dose selector 140 is rotated. This is achieved via a spur gear feature 134 within the transfer sleeve 130 engaging with a gearbox 65 to a sprocket 66 which indexes the corresponding number belt 61. The second number belt 62 may be indexed by coupling a secondary feature (protrusion 136) on the transfer sleeve 130 to an additional gearbox or directly to the second belt 62. In the embodiment shown in FIGS. 8 to 10, the first number belt 61 may be provided with numbers "0" to "9" twice, and the second number belt 62 may have the numbers "0" to "12" thereon. Instead of the "0" on the second belt 62, a blank may be provided. In other words, for every full rotation of dose selector 140 the first belt 61 (the single units counter belt) makes a full revolution displaying the numbers "0" to "9" twice. At the same time, the second belt 62 (ten units counter belt) intermittently moves between two positions, for example from blank to "1" and from "1" to "2" and so on. Starting from zero units dialled, a full revolution of dose selector 140 will result in a display showing "2" on the second belt 62 and "0" on the first belt 61, such that belts 61 and 62 together display "20".

When the injection button 70 is pressed the following actions take place which can be understood comparing FIGS. 16a to 16c (button 70 released) with FIGS. 17a to 17c (button 70 pressed):

The driver 40 is moved forward by the injection button 70 and disengages from the last dose sleeve 120. The last dose protection nut 110 thus remains static throughout an injection. Further, the driver 40 begins to compress the return spring 150 and engages with the lead screw drive nut 100 via clutch teeth 42, 102. At this point the driver 40 is still engaged with the energy storage ratchet 13, 44 to prevent the torsion spring 90 from unwinding. The driver 40 disengages from the dose selector 140 which may now be rotated freely without influencing injection or dial dose. Over the last 1 mm or so the driver 40 becomes fully engaged with the drive nut 100 and moves off the energy storage ratchet 13, 44. The torsion spring 90 begins to unwind rotating the driver 40 which in turn spins the drive nut 100. As the drive nut 100 rotates the piston rod 30 (lead screw), which is splined to the device outer housing 10, moves forwards dispensing the medication.

Dose interruption and dose splitting is possible. If the axial force on the injection button 70 is removed, the button 70 returns to its initial axial position relative to the dose selector 140 under the action of return spring 150. This allows the ratchets 44 on the driver 40 to engage with the splines 13 of the outer housing 10, thus preventing further injection due to the driving torque of the torsion spring 90. Further, this reengages the driver 40 with the dose selector 140 and the last dose sleeve 120, thus allowing the user to adjust the remaining set dose upwards or downwards by rotating the dose selector 140. At this point the dose selector 140 will realign with the outer housing 10 as explained below. The dose can be changed by rotating the dose selector 140 and pressing the button 70 restarts the injection manoeuvre.

During injection the torsion spring 90 will unwind, rotating the driver 40. This will index the dose number mechanism such that the number counts down towards "0". At the same time the nut 50 moves back towards its "0" position. When the nut 50 has reached this position the user will hear and/or feel a "click" to signify end of injection. The end of injection is the moment when the plunger stops moving, whereas the end of dose is when the full volume of the drug has been delivered, which could include the hold time. This is achieved by features on both the nut 40 and the transfer sleeve 130 passing over each other with slight detent interference as shown in FIGS. 11 and 12.

Figure 13B:
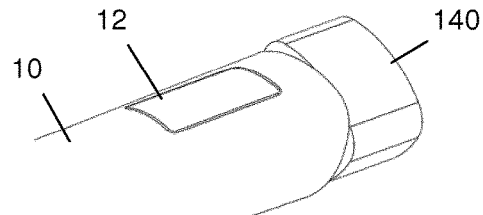

This exemplary embodiment has a non-axisymmetric outer housing 10 and dose selector 140 which means that the dose selector 140 becomes 'misaligned' relative to the outer housing 10 during dose setting. FIGS. 13a and 13b show the dose selector 140 aligned and misaligned, respectively. There is no technical problem with this but users may prefer that the dose selector 140 is realigned to the outer housing 10 at the end of each injection. Therefore the device includes a mechanism for realigning the dose selector 140 with the device outer housing 10 when the user releases the button 70. As depicted in FIGS. 14 and 15, when the user releases the button, the driver 40 moves axially back to its "0"

position. As the driver 40 comes in to contact with the dose selector 140, male location features (splines 45) on the driver 40 begin to engage with corresponding female helical features 142 located within the dose selector 140. This causes the dose selector 140 to rotate until it becomes fully engaged with the driver 40. The dose selector 140 is then fully aligned with the outer housing 10.

Most known pen injectors have a dose indicator which displays the set dose to the user, and counts down to zero as the dose is dispensed. Most pen injectors also feature the rotation of at least one component to set the dose. The dose is normally delivered by converting the rotational movement of setting the dose into translation movement of the bung in the cartridge. Therefore most pen injectors feature a number sleeve with dose indications on it which moves on a helix relative to the body.

The problems with running the number sleeve on a helix relative to the body are that: The number sleeve moves axially which can make the device longer. The minimum axial movement is limited due requirements on the minimum text size and the maximum number of doses which must be supported. Further, devices with a large number of doses will require large axial displacements of the number sleeve, and it is difficult to prevent numbers being shown outside the dose indicator window, for example on the barrel of the number sleeve. In addition, the geometry of the text is tied to the geometry of the drive mechanism. This can limit text size or require large displacements for dose setting and injection.

A benefit of the number belt concept is that the number belts 61, 62 only rotate, they do not move axially. Therefore many of the problems above are avoided. Another advantage of the number belt dose indicator is that the flexible nature of the belt elements allows the dose indicator mechanism to be arranged in a wider range of form factors. In many cases this will allow a more efficient use of space within the device packaging. Additionally the dose number may be presented on a much flatter surface than a cylinder. This allows larger perceived dose numbers and less distortion when viewing at an angle. Should the device require additional magnification, a flatter display will allow greater freedom with the lens design and potentially less optical distortion.

Depending on the size of the maximum dose and the incremental display of individual units a spool based mechanism could be considered. In this variant the belt or tape loop mechanism would be replaced with a spool to spool system. This would allow the dose to be dialled up or down as usual but the dosage range would be limited by the length of the spool as opposed to a looping tape or belt.

The belt does not need to indicate using numbers: the indicator could include, but not be limited to, one or more of the following, perhaps in combination: text, icons, symbols or images, color, braille or other tactile surface.

Currently most injector pens follow an axisymmetric form factor. This is largely dictated by the injection mechanism and also the helical number sleeve. The number belt mechanism offers greater freedom to develop non axisymmetric devices offering improved usability for handling and grip, clearer easier to read dose numbers, and reduced probability of the pen rolling on and falling from an elevated surface such as a table or shelf.

There is also a perceived problem of device differentiation: many pen injectors are indistinguishable from one another which could be a problem for users in identifying the correct device to use for a given use case (for example, selecting between long-acting and short-acting insulin). In addition, there is a commercial problem whereby it is difficult for the manufacturer to explain the advantages of their pen injector to buyers if the buyer cannot distinguish it from competitor pen injectors.

The number belt dose indicator can be used in any device which would benefit from a non-axisymmetric device format or where clearer dose display is desirable. The most relevant applications are in dispensing mechanisms, of which the following list gives a few examples: Drug delivery devices such as pen injectors or autoinjectors; medical devices such as dispensers of antiseptic creams, analgesic creams, detergents and so on; devices for dispensing adhesives, lubricants, paints, detergents and suchlike (These could be used in professional applications such as engineering workshops or in consumer applications such as 'Do It Yourself' products or 'Fast Moving Consumer Goods'.); food dispensers for non-rigid foods such as tomato sauce, crushed garlic, cheese, butter, juice, smoothie, soup, coffee, tea, jam, peanut butter and so on.

The invention claimed is:

1. A drug delivery device for selecting and dispensing a number of user variable doses of a medicament, the drug delivery device comprising:
    an outer housing comprising a cylindrical portion;
    a dosing element which rotates in a first direction during dose selecting;
    a display for indicating a selected dose, wherein the display comprises at least one belt having symbols, colors, or texture for indicating the selected dose, the at least one belt being coupled to the dosing element such that a rotation of the dosing element spools the at least one belt, wherein the dosing element rotates in a second, opposite direction during dose dispensing; and
    a striker plate having a curvature less than a curvature of the cylindrical portion of the outer housing, wherein a portion of the at least one belt is simultaneously guided on the striker plate and visible through the outer housing.

2. The drug delivery device of claim 1, wherein the at least one belt is directly coupled to the dosing element.

3. The drug delivery device of claim 2, wherein the dosing element comprises a sprocket and wherein the at least one belt engages the sprocket.

4. The drug delivery device of claim 2, wherein the at least one belt is coupled to the dosing element such that a continuous rotation of the dosing element is translated into an intermittent motion of the belt.

5. The drug delivery device of claim 1, wherein the at least one belt is indirectly coupled to the dosing element.

6. The drug delivery device of claim 5, wherein the dosing element comprises at least one drive gear which is coupled to a sprocket and wherein the at least one belt engages the sprocket.

7. The drug delivery device of claim 1, wherein the at least one belt comprises:
    a belt which is directly coupled to the dosing element; and
    a further belt which is indirectly coupled to the dosing element.

8. The drug delivery device of claim 7, wherein the belt is coupled to the dosing element such that a first continuous rotation of the dosing element is translated into an intermittent motion of the belt, and wherein the further belt is coupled to the dosing element such that a second continuous rotation of the dosing element is translated into a continuous motion of the further belt.

9. The drug delivery device of claim 1, wherein the striker plate forms a flat or arced plane.

10. The drug delivery device of claim 1, wherein the at least one belt forms a closed loop.

11. The drug delivery device of claim 1, wherein the at least one belt has two ends each being attached to a spool.

12. The drug delivery device of claim 1, further comprising:
a housing;
a cartridge holder for retaining a cartridge containing the medicament;
a piston rod displaceable relative to the cartridge holder;
a driver coupled to the piston rod; and
at least one clutch, wherein the at least one clutch decouples the driver and the dosing element during dose selecting and couples the driver and the dosing element during the dose dispensing.

13. The drug delivery device of claim 1, further comprising a spring configured to drive the dosing element during the dose dispensing.

14. The drug delivery device of claim 1, further comprising a cartridge containing a medicament.

15. The drug delivery device of claim 1, wherein the at least one belt comprises a belt and at least one further belt, each of the belt and the at least one further belt having symbols for indicating the selected dose, wherein the belt and the at least one further belt are coupled to each other via a transmission or gearing such that a continuous motion of the belt is translated into an intermittent motion of the at least one further belt.

16. The drug delivery device of claim 1, wherein a drive for the at least one belt is derived from one or more other belts or sprockets, either directly or indirectly.

17. A drug delivery device for selecting and dispensing a number of user variable doses of a medicament, the drug delivery device comprising:
an outer housing comprising a cylindrical portion;
a dosing element which rotates in a first direction during dose selecting;
a display for indicating a selected dose, wherein the display comprises at least one belt having symbols, colors, or texture for indicating the selected dose, the at least one belt being coupled to the dosing element such that a rotation of the dosing element spools the at least one belt, wherein the dosing element rotates in a second, opposite direction during dose dispensing; and
a striker plate having a curvature less than a curvature of the cylindrical portion of the outer housing, wherein the at least one belt is guided on the striker plate,
wherein the at least one belt comprises:
a belt which is directly coupled to the dosing element, and
a further belt which is indirectly coupled to the dosing element,
wherein the belt is coupled to the dosing element such that a first continuous rotation of the dosing element is translated into an intermittent motion of the belt, and wherein the further belt is coupled to the dosing element such that a second continuous rotation of the dosing element is translated into a continuous motion of the further belt.

* * * * *